(12) United States Patent
Lemke et al.

(10) Patent No.: US 8,700,422 B2
(45) Date of Patent: Apr. 15, 2014

(54) APPARATUS AND METHODS FOR MEDICAL PATIENT ROLE PLAYING/SIMULATION ACTIVITY

(75) Inventors: Gibert Lemke, Los Gatos, CA (US); Debra Lieberman, Santa Barbara, CA (US); Tadashi Egami, Belmont, CA (US)

(73) Assignee: Koninklijke Philips N.V., Eindhoven (NL)

( * ) Notice: Subject to any disclaimer, the term of this patent is extended or adjusted under 35 U.S.C. 154(b) by 869 days.

(21) Appl. No.: 12/599,822

(22) PCT Filed: May 14, 2008

(86) PCT No.: PCT/IB2008/051899
§ 371 (c)(1),
(2), (4) Date: Nov. 12, 2009

(87) PCT Pub. No.: WO2008/142611
PCT Pub. Date: Nov. 27, 2008

(65) Prior Publication Data
US 2010/0274575 A1    Oct. 28, 2010

Related U.S. Application Data

(60) Provisional application No. 60/938,280, filed on May 16, 2007.

(51) Int. Cl.
*G06Q 10/00* (2012.01)
*G06Q 50/00* (2012.01)
*A63F 13/00* (2006.01)

(52) U.S. Cl.
USPC .................................... 705/2; 705/3; 463/1

(58) Field of Classification Search
USPC ................... 128/897; 463/4, 1; 705/2–3
See application file for complete search history.

(56) References Cited

U.S. PATENT DOCUMENTS

| | | | |
|---|---|---|---|
| 5,006,987 A | 4/1991 | Harless | |
| 5,918,603 A * | 7/1999 | Brown | 128/897 |
| 2003/0022141 A1 | 1/2003 | Packard | |
| 2006/0105825 A1* | 5/2006 | Findlay | 463/4 |
| 2006/0272652 A1 | 12/2006 | Stocker et al. | |
| 2007/0293315 A1* | 12/2007 | Mizuta | 463/36 |

FOREIGN PATENT DOCUMENTS

| | | |
|---|---|---|
| WO | 0118771 A2 | 3/2001 |
| WO | 2007057793 A2 | 5/2007 |
| WO | 2007117719 A2 | 10/2007 |
| WO | 2008107811 A1 | 9/2008 |

* cited by examiner

*Primary Examiner* — Joseph Burgess

(57) ABSTRACT

A health care apparatus (10) and methods for rendering audio visual content to a medical patient in the patient's home, in which a content element storage (22) stores a plurality of audio visual content elements (28) to be rendered to the patient, including role playing simulation content elements (40) in which in which the patient is presented with a situation involving an issue related to a medical condition confronted by a character (42) and in which the patient provides input related to the character's situation.

20 Claims, 6 Drawing Sheets

FIG. 5

14 — Welcome to the Motiva Personal Healthcare Channel

FIG. 6

14 — Please enter your Code number
X X X

FIG. 7

14 — Good Morning
Bruce Thomas

FIG. 8

14 — Today's Activities:
o Watch video
o Situation of the Day
o Take Survey or Quiz
o Main menu
o Press any key to begin

FIG. 9

14 — Today's Video:
Hypoglycemia
Run time:        6 min.
Point value: 1 point
This video covers the Causes, prevention, and treatment of Hypoglycemia (low blood glucose)

FIG. 10

14 — Playing Video
Hypoglycemia

FIG. 11

14 — Save Video?
Would you like to save this video so that You can view it again another day?
☑ Yes, save it
☐ No, don't save it

FIG. 12

14 — Today's Activities:
☑ Watch video
o Situation of the Day
o Take Survey or Quiz
o Main menu
o Press any key to begin Situation of the Day:

Feeling Dizzy

FIG. 13

Select Character

 

☑ Mary ☐ Bill

FIG. 14

Mary introduces herself

FIG. 15

Check up on Mary
This morning, Mary is feeling a little dizzy.

To continue, press ☐

FIG. 16

When Mary took her blood glucose reading, it was 68 mg/dl.
What should Mary do?

☐ Fast for 15 minutes
☑ Drink a glass of fruit juice
☐ Exercise
☐ Take a nap

FIG. 17

Correct!
One small serving of fruit juice can raise Mary's blood glucose to a normal level.

To continue, press ☐

FIG. 18

Mary Thanks You!

FIG. 19

Congratulations!
   You've finished your current goal:
   Understanding Diabetes.

Press any key for More options

FIG. 20 ent storage and the itinerary arrangement system may be part of

APPARATUS AND METHODS FOR MEDICAL PATIENT ROLE PLAYING/SIMULATION ACTIVITY

INCORPORATION BY REFERENCE

The following patent applications are hereby incorporated by reference in their entireties: U.S. Patent Application Ser. No. 60/738,104, filed Nov. 17, 2005, entitled "REMOTE DIAGNOSTICS FOR IN-HOME AUDIO VIDEO GEAR"; U.S. Patent Application Ser. No. 60/714,414, filed Apr. 7, 2006, entitled "SELF-ADAPTIVE CARE PLAN GOAL MODULES"; U.S. Patent Application Ser. No. 60/804,587, filed Jun. 13, 2006, entitled "SELF-ADAPTIVE CARE PLAN GOAL MODULES"; and U.S. Patent Application Ser. No. 60/893,739, filed Mar. 8, 2007, entitled "LOW COST SYSTEM FOR REMOTE PATIENT AUDIO/VIDEO CONTENT DELIVERY".

DESCRIPTION

The following relates to ongoing health care for patients with medical conditions such as chronic illnesses, long term medical conditions, etc., and for teaching prevention behaviors to healthy patients. In particular, this application relates to involving medical patients in simulation/role playing activities in conjunction with provision of information regarding management of their medical condition or prevention of potential medical conditions. The patient is provided with information and participates in the activities in the patient's home or other location remote from a health caregiver via a secure, personalized platform service that connects patients that may not be technologically savvy with their care team to facilitate the healthcare organization's effective and efficient empowerment and assistance of patients in managing their health and lifestyle. The patient is apt to make better choices in dealing with their health condition or prevention behaviors if provided with appropriate information and vicarious experience in managing health. Moreover, the patient is more likely to continue using the program when they are engaged through role playing simulations, without which the patient may become bored with the program. The application allows the patient to practice how to deal with a variety of scenarios related to a medical condition or prevention behavior to enhance development of the necessary decision making skills needed in real life, where repetition through dealing with similar situations can reinforce knowledge and the decision-making process. The role playing simulations portray role-model characters going through the same or similar experiences so that patients benefit from observation learning and from knowing that they are not alone in coping with their illness.

Treatment of a medical condition and prevention of future conditions can be assisted through modifying the patient's behavior in one or more respects, such as encouraging proper diet and/or exercise, cessation of undesired activities, etc, where patients may respond positively to pertinent information offered in the context of helping other persons who are undergoing the same experiences in coping with the same or similar medical problems. Further, patients find hope in knowing that they are not alone and that others in the same circumstances can meet with success by learning simple techniques and strategies for getting along. Patients with chronic diseases, however, may have limited mobility, and it may be difficult or impossible to get out and participate in live peer group discussions, particularly on a regular basis. Interactive role playing simulations, such as in an on-going quiz or game that may be incorporated into an interactive healthcare program used with a computer, a television, or other form of audio visual rendering and user input devices can provide simulation, role-playing, and repetition as a form of education in an applied way. The system employs video presentations and teaching surveys as a way to convey information to patients, together with simulated situations involving giving a friendly, appealing character advice on how to deal with health issues that will arise in their daily life. The simulation aspect allows the patient to make decisions (and mistakes) without dangerous consequences in the context of aiding a friend, so as to engage the patient to increase effectiveness and knowledge retention in the patient.

In accordance with one aspect, a health care apparatus is provided to render audio visual content to a medical patient. The apparatus includes a content storage that stores audio visual content elements to be rendered to a medical patient as part of a defined care plan. The content elements include role playing simulation content in which the patient is presented with a situation involving an issue related to a medical condition confronted by a character and the patient provides input related to the character's situation. The apparatus further includes an itinerary arrangement system operatively coupled with the content element storage, which selects content elements from the storage including at least one role playing simulation content element to be rendered to the patient in a given viewing session as part of a defined care plan for the patient. In addition, the apparatus includes a user interface coupled with the network and with a display device, where the user interface is operable by the patient to render the selected content elements to the patient via the display device. The apparatus may advantageously arrange the content elements into a serially ordered itinerary for presentation to the patient with the role playing simulation content element presented to the patient after an educational content element to reinforce patient learning and to stimulate patient engagement in their care plan. A character selection content element may be presented including images and names for two or more characters to allow the patient to select a character for the role playing simulation activity and a character introduction content element may be rendered including an image of the selected character and information, such as audio of the selected character introducing himself or herself to the patient. The role playing simulation content elements may further include a response rendered to the patient after the patient answers the question to indicate the correct answer along with an image to reinforce the correct answer, and an image of the character may be displayed to thank the patient for their help to the character.

In another aspect, a method is provided for rendering health care information to a patient. The method comprises storing audio visual content elements to be rendered to a medical patient including a plurality of role playing simulation content elements in which the patient is presented with a situation involving an issue related to a medical condition confronted by a character and in which the patient provides input related to the character's situation. The method further includes selecting one or more stored content elements based at least partially on the patient's medical condition, where the selected content elements include one or more role playing simulation content elements to be rendered to the patient in a given viewing session as part of a defined care plan. The method also provides for arranging the selected content elements into a serially ordered itinerary with the at least one role playing simulation content element arranged to correspond to a chronology of the defined care plan, and rendering a display of the selected content elements to the patient. The content selection may comprise selecting at least one educational content element to be rendered to the patient prior to the role playing simulation content, as well as selection of character selection and character introduction content elements to be presented before the role playing simulation activity. The role playing simulation content element presentation may also include a response including an indication of the correct answer following the patient's answer, along with an image to reinforce the correct answer and an image of the character thanking the patient.

In yet another aspect, a method of providing health care to a patient is presented, including defining a care plan with features to assist the patient with defined health issues, and providing a role playing session as part of the care plan. The provision of the role playing session can comprise presenting a situation to the patient involving an issue related to a medical condition confronted by a character, receiving input from the patient regarding a solution to the character's situation, and presenting a response to the patient's input including an indication of a correct solution and an image to reinforce the correct solution.

In still another aspect, a method is provided for facilitating patient education regarding a medical condition. The method comprises presenting educational content to the patient about a medical topic via a user interface operatively coupled with a display device that renders preselected content elements to the patient as part of a defined care plan, and reinforcing the educational content by engaging the patient in a role playing simulation in which the patient provides input to the user interface to assist a character with a situation involving an issue related to the medical topic confronted by the selected character. The method may further comprise presenting a response to the patient's input with an indication of a correct solution and an image to reinforce the correct solution.

These techniques allow the patient to experience many or all of the advantages of role playing simulation activities without having to leave their home. Still further advantages of the present disclosure will be appreciated to those of ordinary skill in the art upon reading and understand the following detailed description.

The present subject matter may take form in various components and arrangements of components, and in various steps and arrangements of steps. The drawings are only for purposes of illustrating preferred embodiments and are not to be construed as limiting the subject matter, wherein:

FIG. 5 is a schematic diagram illustrating an exemplary startup screen rendered to a patient using the apparatus of FIG. 1;

FIG. 6 is a schematic diagram illustrating an exemplary login screen rendered to a patient using the apparatus of FIG. 1;

FIG. 7 is a schematic diagram illustrating an exemplary welcome screen rendered to a patient using the apparatus of FIG. 1;

FIG. 8 is a schematic diagram illustrating an exemplary itinerary screen rendered to a patient using the apparatus of FIG. 1;

FIG. 9 is a schematic diagram illustrating an exemplary content overview screen rendered to a patient using the apparatus of FIG. 1;

FIG. 10 is a schematic diagram illustrating an exemplary content viewing screen rendered to a patient using the apparatus of FIG. 1;

FIG. 11 is a schematic diagram illustrating an exemplary content save option screen rendered to a patient using the apparatus of FIG. 1;

FIG. 12 is a schematic diagram illustrating an exemplary itinerary screen with a partially complete itinerary rendered to a patient using the apparatus of FIG. 1;

FIG. 13 is a schematic diagram illustrating an exemplary situation of the day introduction screen rendered to a patient using the apparatus of FIG. 1;

FIG. 14 is a schematic diagram illustrating an exemplary character selection content screen rendered to a patient using the apparatus of FIG. 1;

FIG. 15 is a schematic diagram illustrating an exemplary character introduction screen rendered to a patient using the apparatus of FIG. 1 in which a selected character introduces herself;

FIG. 16 is a schematic diagram illustrating an exemplary situation of the day role playing simulation screen rendered to a patient using the apparatus of FIG. 1 in which the selected character's situation is presented to the patient;

FIG. 17 is a schematic diagram illustrating another exemplary situation of the day role playing simulation screen rendered to a patient using the apparatus of FIG. 1 in which a question is posed to the patient regarding the character's situation and in which the patient provides an answer to the question;

FIG. 18 is a schematic diagram illustrating another exemplary situation of the day role playing simulation screen rendered to a patient using the apparatus of FIG. 1 in which the correct answer is given to the patient along with an image to reinforce the correct answer;

FIG. 19 is a schematic diagram illustrating another exemplary role playing simulation screen rendered to a patient using the apparatus of FIG. 1 including an image of the character thanking the patient;

FIG. 20 is a schematic diagram illustrating an exemplary congratulatory screen rendered to a patient using the apparatus of FIG. 1;

Figure 1:
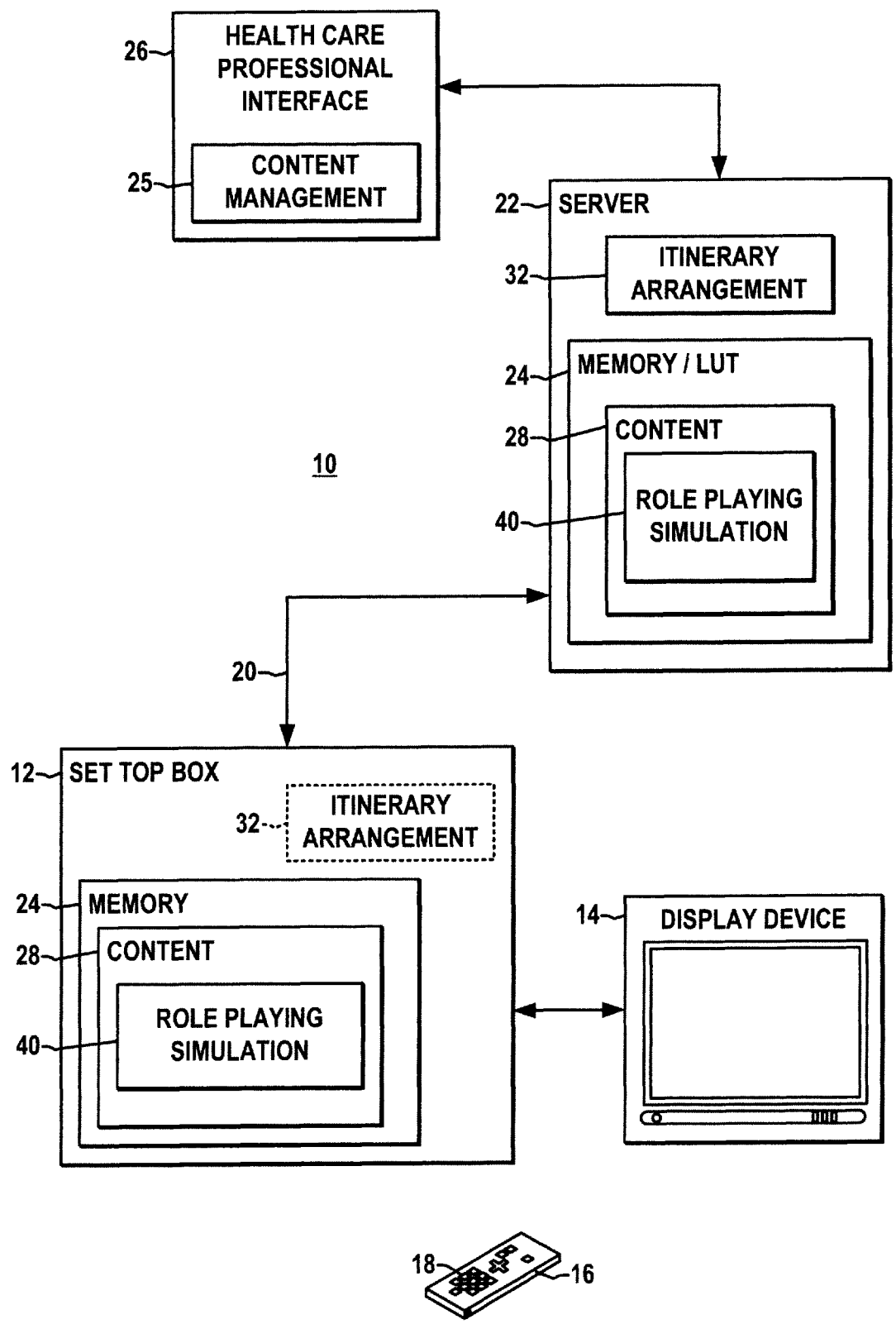
FIG. 1 is a schematic diagram illustrating an exemplary patient healthcare apparatus network in which one or more aspects of the present disclosure may be implemented.

FIG. 1 shows an exemplary health care apparatus 10 which operates to present or render audio visual role playing simulation content elements to medical patients. Patients with one or more medical conditions often have lifestyle issues which complicate the medical issues, for instance, improper diet, lack of exercise, obesity, smoking, etc. can aggravate diabetes or other medical problem. The apparatus 10 may be advantageously employed to assist patients in managing their disease, adjusting their lifestyle and other behavior modification by providing each patient with personalized programming that can be presented in the patient's home or other convenient setting. In one exemplary implementation, the patient is provided with a care plan in the form of a series of educational or motivational programs directed to healthcare issues specific to that particular patient and their medical condition(s), where the programs include one or more content elements 28. A given patient might be provided, for instance, with educational and motivational programming at the same time each day to assist the patient in establishing and maintaining a diet and exercise regimen. The programming may be provided in any suitable form and format, such as a video disc (e.g., DVD or other format), from a programming memory, or from a central source, such as a content element storage of a networked server 22 operated by a hospital or medical care facility that has prescribed the programming to provide a predetermined care plan, and the content 28 is transferrable over and/or selectively operable via a public communications network 20 to the patient's home. A set top box or other user operable interface 12 is provided in the patient's home, which decodes the signals intended for the specific patient and displays the corresponding programming on the patient's television or other suitable display device 14 operatively associated with the user interface 12. The patient can interact with the apparatus 10 using their TV or set top box remote controller 16, where the set top box user interface 12 provides for user feedback, such as weigh-ins, blood pressure readings, user selections, etc. to be communicated from the patient to the healthcare facility. In other implementations, the apparatus 10 can be located in a clinic, hospital, school, work site, community center, or other public or private place.

Medical patients often need to continue a regimen of exercise, dieting, lifestyle change, etc. after the patient leaves a hospital and has completed doctor visits normally associated with the patient's condition. For example, when a physician prescribes short term care such as a finite amount of prescription drugs, rest, and the like, once the patient takes all the pills, etc., the treatment is in one sense complete. The patient may alternatively be diagnosed with a long term illness or chronic disease or other medical condition that requires long term care and/or lifestyle changes, in which case the healthcare professional may prescribe habits or behaviors that were not previously a part of the patient's daily routine. Motivated by the visit with the doctor, the patient may start the new treatment with good intentions, but may gradually fall back into the prior lifestyle as time goes by. In one example, a doctor may instruct a diabetes patient to eat better, exercise more, and check their insulin levels regularly. Absent further doctor visits or other reminders or motivations, however, the patient may eventually revert to previous habits by forgetting to diet and exercise, and possibly foregoing regular glucose measurements.

As shown in FIG. 1, the exemplary health care apparatus 10 helps to maintain continuing patient motivation by providing a dynamic care giving experience in the patient's home or other convenient location, which the patient can utilize long after any given visit to a doctor. The system may further provide health related feedback from the patient to the caregiver, such as blood pressure values, glucose levels, etc. The apparatus 10 includes one or more individual user interface devices 12, one of which is illustrated in FIG. 1, and which can be in the form of a set top box, processor, or other such interface device that is operable by the patient user and which is operatively coupled with the network 20. The user interface 12, moreover, is operatively associated with a display 14, such as the patient's television set, a monitor, or other display device by which audio visual content 28 can be presented or rendered to the patient. In one implementation, the patient logs on to the apparatus 10 via the interface device 12, using a handheld remote control device 16, entering information via one or more keys or buttons 18 thereof. The interface 12 may be a separate set top box connected to the display 14 via suitable cables as shown, or the display 14 may be integrated into the interface 12. The interface device 12 interacts with the input device 16, such as a handheld remote, touch screen, keyboard, mouse, or other similar device by which the patient can enter information, such as passwords, responses to questions, health related readings such as weight or blood pressure, etc. The input device 16 may preferably include large keys 18 with distinct markings such as color, shape, and/or labeling that clearly delineate the intended use or functionality to a patient.

The interface device 12 is operatively coupled with the public network 20, which can be any suitable network, whether wired or wireless or combinations thereof, for example, such as an interactive cable TV network, the internet, etc. Although acting over a public or private network 20, the user interface device 12 communicates with encrypted signals over a secure layer of the network 20 to protect sensitive information of the patient. The interface 12 communicates via the network 20 with various servers such as a server 22 that is remote from the patient location and which preferably is operated by the patient's health care provider, hospital, associated service organization, etc. The server 22 stores information and/or data and in one example includes a memory such as a look-up-table or database 24 of patient care plans that have been synthesized for all the patients for which this particular server 22 is responsible. A care plan is preferably synthesized by a nurse manager, doctor, or other health care professional based on the patient's medical history. To create a care plan, the health care professional reviews the patient's medical history, and inputs information to a generic care plan template. The system also includes a content management system 25 for uploading, versioning, and pre-viewing content for the health care professional. The content management system 25 also includes a facility to experience what the patient would actually see before actually deploying the media content 28 to the patients.

The health care professional in one embodiment inputs the information to a template via a user interface 26 operatively coupled with the server 22. The templates act as road maps to direct the health care professional in developing the care plan, ensuring that all appropriate questions are addressed. In addition to the template, the health care professional can add features to the care plan based on physician's notes, personality traits of the patient, etc., to further tailor each care plan to an individual patient. The patient's clinician may also have a means such as user interface 26 to see the patient's daily list of media elements to be completed, and may determine when each media item was started, stopped, and status (unopened, in progress, complete, etc.). One, some or all of these factors can be used by the health care professional in initially designing the patient's care plan, or modifying the care plan after the commencement of the care plan.

The server 22 uses the template to compile a care plan for the patient. The server 22 in one embodiment selects specific content elements 28 (videos, surveys, still pictures, audio files, requests for patient input, role playing simulations 40, etc.) that will be a part of the patient's care plan. The server 22 also decides in what general order the content should be presented to the patient, although the care plan designer has the option to order the content elements 28 differently, based on type of content, topic, and/or other factors. The care plan designer has the ability to edit media files or the logical branching between files to improve the narrated experience that accompanies the care plan elements on the patient's user interface device 12, including the selective presentation of the role playing simulation content 40. The server 22 in one embodiment is in periodic communication with the set top box 12 of a particular patient and receives information and feedback about the patient's progression through the prescribed material on an on-going basis, and may select new content elements for presentation to the patient as they become appropriate. For example, a diabetic patient may initially receive general and overview information about diabetes and as the patient progresses through that material, the server 22 will select more detailed and specific content directed to the particular patient based both on the care plan template and progress and understanding of the patient. Moreover, the patient may be selectively provided with certain interactive role playing simulation content elements 40 that are scheduled in coordinated fashion with other related content items 28 (e.g., informational and/or survey/quiz content 28), and the selection and/or placement of the simulation content 40 in certain implementations can be based at least partially on the patient's responses to survey/quiz questions, input values relating to the patient's condition, etc.

An itinerary arrangement system or component 32, such as hardware, software, or combinations thereof, is provided in the server 22. The system 32 selects content elements 28 and arranges these in an ordered presentation for a given patient viewing session as part of a defined care plan. In other possible implementations, an itinerary arrangement system 32 can be provided as part of the user interface 12, and the interface 12 may also comprise a content element storage memory 24 holding one or more content items 28 including role playing simulation content 40, as well as preassembled care plans, where the health care provider may selectively modify the preloaded plans via the interface 26 and the content management system 25 through communications across the network 20. In such an implementation, the patient may be provided with a set top box 12 preloaded with the content 28 constituting a care plan, with the health care provider being able to access the interface 12 via the network 20 to make schedule changes, arrange content, download further content to the interface 12, etc.

The memory 24 in the server 22 and/or the content storage capacity of the memory 24 in the user interface set top box 12 provide a content element storage coupled with the network 20 for storing a plurality of audio visual content elements 28 including role playing simulation elements 40 to be selectively rendered to a medical patient. An itinerary arrangement system 32 of the server 22 or the user interface 12 is operatively coupled with the content element storage 24 and operates to select one or more content elements 28 from the content element storage 24 including at least one role playing simulation element 40 to be rendered to the patient in a given viewing session based at least partially on the patient's medical condition, where the itinerary arrangement system 32 is preferably adapted to obtain information regarding the patient's medical condition from the content element storage in making the content selection.

The user interface 12 is also coupled with the network 20 and the display device 14, and is operable by the patient to render the selected content elements 28 to the patient via the display device 14. In one exemplary implementation, moreover, the itinerary arrangement system 32 arranges the selected content elements into a serially ordered itinerary for presentation to the patient with the role playing simulation content element(s) 40 presented to the patient after an educational content element. Furthermore, the arrangement system 32 may order the content elements such that a role playing simulation content 40 is presented after an interactive survey/quiz content element, and the role playing simulation content elements 40 can be selected based at least partially on a patient response to an interactive survey or quiz content element 28 in a given viewing session. As illustrated and described further with respect to FIG. 14 below, the itinerary arrangement system 32 may allow the patient to select from a list of characters 42 who will be the subject of situation of the day type role playing simulations 40. By using a character 42, the role playing simulation activity enhances the patient's experience and the goals of patient learning and/or behavior modification by having issues related to the patient's condition presented and reinforced in the context of a person having characteristics similar to the particular patient.

In the illustrated implementation, the role playing simulation content elements 40 are stored along with other types of audio visual content elements 28, such as educational content segments, survey/quiz type interactive content elements, etc., from which a care program can be constructed for a given patient and from which individual viewing sessions can be arranged. One or more content elements 28 are selected from the content element storage 24 based at least partially on the patient's medical condition, where the selected content elements 28 include at least one simulation 40 to be rendered to the patient in a given viewing session as part of the defined care plan. The content elements 28 and 40 can also be selected based on other considerations, such as general patient background information, the patient's personal information, such as age, gender, progress through a defined care plan, and the like. The selected content elements 28 and 40 are arranged into a serially ordered itinerary for presentation to the patient, where the ordering may be subject to modification as a viewing session progresses, for example, wherein certain patient responses may trigger the arrangement system 32 to select an interactive simulation 40 for presentation to the patient. For example, if a patient enters an incorrect answer to a survey or quiz element question, a specific role playing simulation 40 may help to show the patient the correct answer in a friendly way, thus helping to educate the patient while providing the positive reinforcement of having a selected character 42 explain an issue or reinforce the importance of a given survey response in a simulated real life situation.

Figure 2:
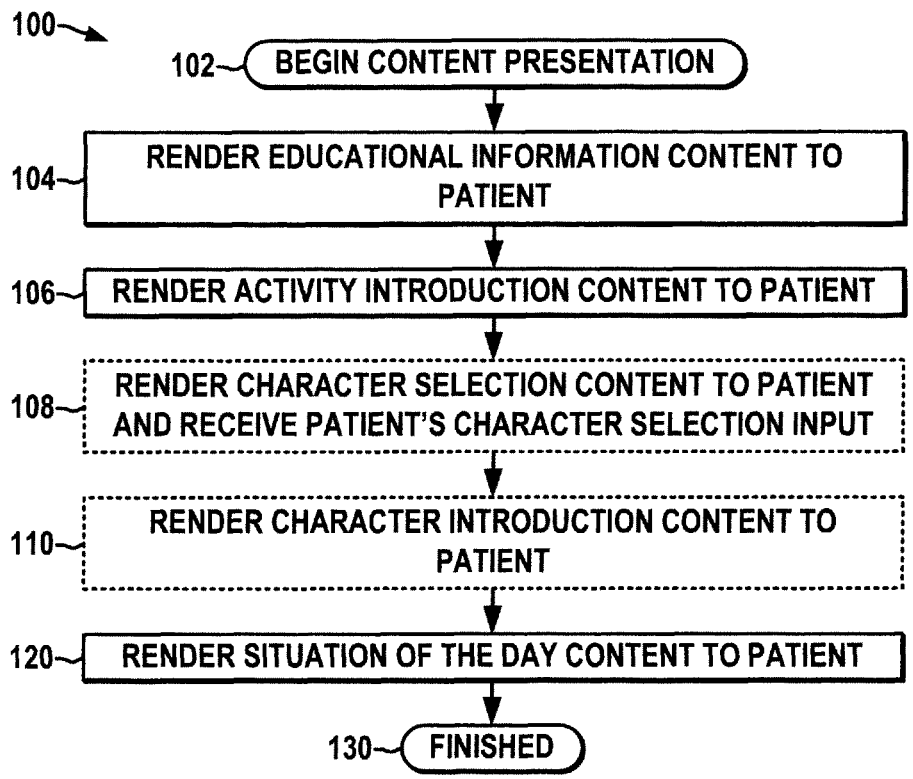
FIG. 2 is a flow diagram illustrating an exemplary method for rendering content to a medical patient including educational information and role playing simulation content according to the disclosure.
Figure 3:
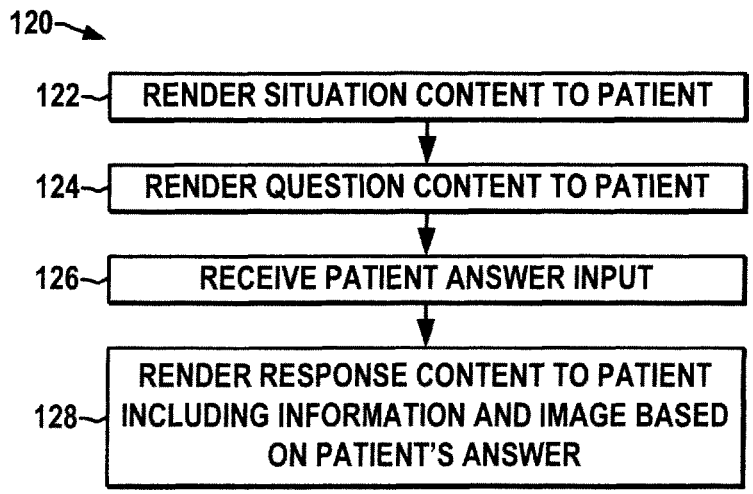
FIG. 3 is a flow diagram illustrating presentation of exemplary "situation of the day" role playing simulation content to a patient according to the disclosure.
Figure 4:
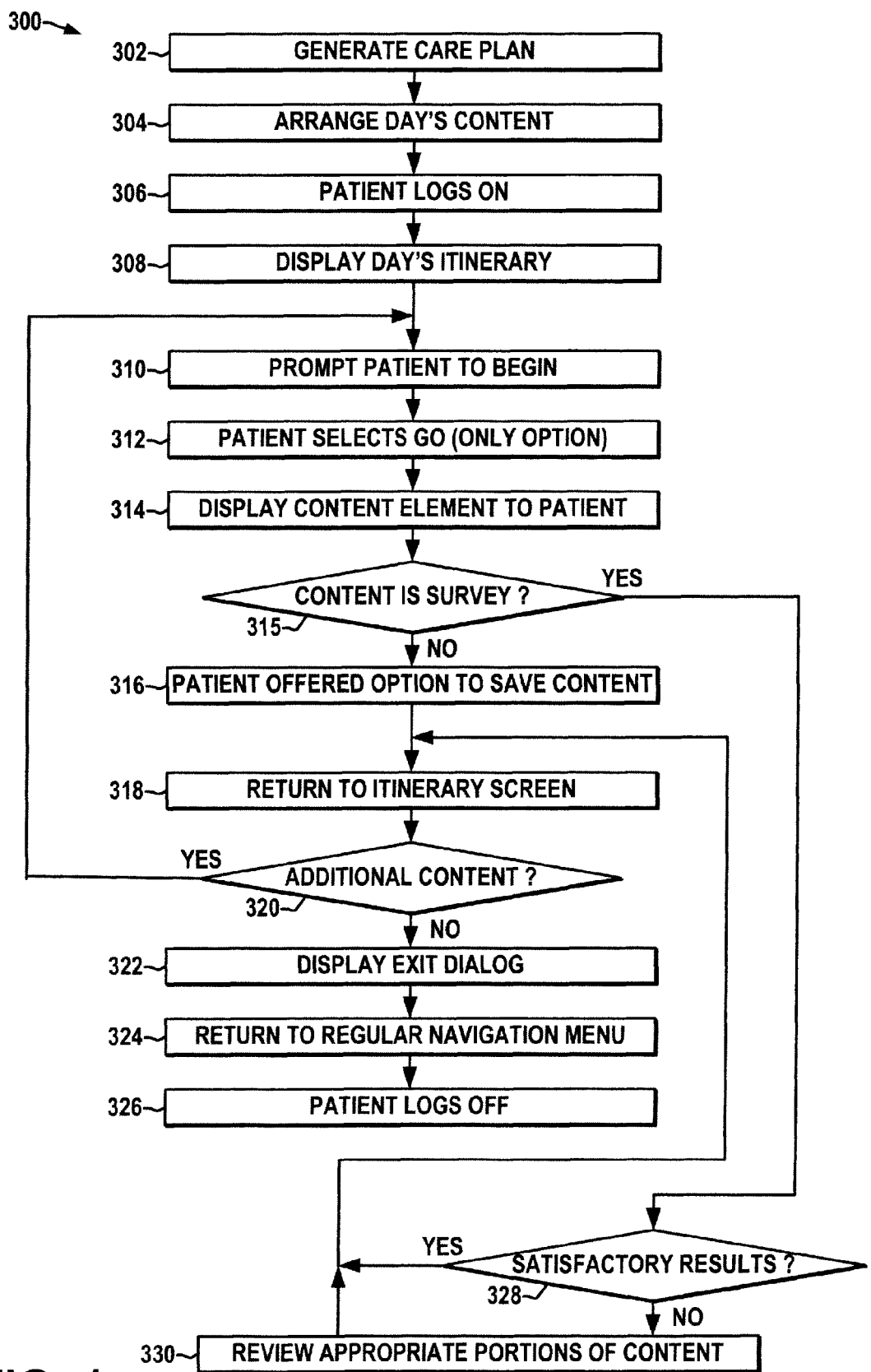
FIG. 4 is a flow diagram illustrating exemplary operation of the apparatus of FIG. 1 in a guided encounter.

As further shown in FIGS. 2-4, the disclosure provides role playing simulation type content 40 to a patient to facilitate patient learning, behavior modification, and motivation while allowing the patient to experience the content in their own home at a time convenient to the patient. FIG. 2 illustrates an exemplary method 100 for rendering content to a medical patient including educational information and role playing simulation content according to the disclosure; FIG. 3 depicts presentation of exemplary "situation of the day" role playing simulation content 120 to a patient according to the disclosure; and FIG. 4 illustrates exemplary operation 300 of the apparatus 10 of FIG. 1 in a guided encounter. Although the methods 100, 120, and 300 are illustrated and described in the form of a series of acts or events, it will be appreciated that the various methods of the disclosure are not limited by the illustrated ordering of such acts or events except as specifically set forth herein. In this regard, except as specifically provided hereinafter, some acts or events may occur in different order and/or concurrently with other acts or events apart from those illustrated and described herein, and not all illustrated steps may be required to implement a process or method in accordance with the present disclosure. The illustrated methods may be implemented in hardware, software, manually, or combinations thereof, whether in a network server 22, in the patient user interface device 12, or in other components of the apparatus 10 or the methods may be implemented in distributed form in two or more components or systems, wherein the disclosure is not limited to the specific devices, systems, applications, and implementations illustrated and described herein.

Referring to FIGS. 1 and 2, the exemplary apparatus 10 employs the simulation content 40 in a structured manner beginning at 102, with the selected content elements 28, 40 being rendered or displayed to the patient generally via the display device 14 associated with the user interface 12 (FIG. 1). In the example of FIG. 2, educational content elements 28 are rendered initially to the patient at 104, followed by activity introduction at 106, optional character selection and introductions at 108 and 110, and situation of the day type role playing activities at 120. Before participating in a simulation activity 120, the patient in this embodiment is presented with medical information, such as informative, educational video or other materials at 104. In other embodiments, other content 28 can be provided prior to the role playing 120, such as interactive quiz/survey type content, for which the role playing simulation provides reinforcement. After presentation of the educational content 28, the upcoming role playing simulation activity is briefly explained to the patient at 106, as illustrated and described further below with respect to FIG. 13. Thereafter, the patient may optionally be provided with a character selection feature at 108 that presents a list of two or more different fictional characters 42 that they would like to follow, which may include a photo or other image along with a brief description of each character as shown below in FIG. 14. The patient then selects one of these characters 42 according to personal preference. The patient will thereafter follow that character 42 through a variety of experiences and decisions over a period of time. The pool of characters 42 from which the patient selects at 108 may be predetermined so as to have similar characteristics to the patient with respect to age, gender or other factors, in addition to the fact that the patient and the characters 42 have the same or similar medical condition(s). Once the character 42 has been chosen by the patient, the patient may also be provided with a short video at 110, such as images and/or text introducing their selected character 42 (FIG. 15 below). This character introduction content may optionally show the character 42 talking about themselves and their condition in their home environment to allow the patient to get to know the character 42. Learning about the character 42 may be a one-time, up-front experience, or may build in subsequent sessions.

Referring also to FIG. 2, with the character 42 selected and introduced, the patient is then engaged at 120 in an interactive role playing simulation activity, as shown for example in FIG. 16. The exemplary apparatus 10 provides this content in the form of a "situation of the day" feature that may be included in the patient's daily program or at other periods according to the defined care plan as set by the healthcare provider. In the illustrated implementations, the role playing simulation activity 120 includes three sub-activities, including a situation at 122, a question at 124 and 126, and a response at 128 to the patient's answer. At 122, the patient is presented with situation content, such as an image of the selected character 42 along with a situation described in text and/or audio that the character 42 is experiencing. At 124, a question is rendered to the patient in relation to the character's situation, as illustrated and described further below in connection with FIG. 17. In the preferred embodiments, the question at 124 corresponds to the health related information that has previously been presented via video or some other source at 104 in FIG. 2. In order to optimize the reinforcement of the educational information in a personalized manner, moreover, the question at 124 is applied to the fictional character 42, as if the patient is advising that character 42 on a particular health decision. The patient selects the best answer at 126. At 128, a response is rendered to the patient's selection, regardless of whether the patient's answer was right or wrong, where the response content at 128 may include information and an image to reinforce the correct answer, as shown below in FIG. 18. Thereafter, the remainder of the daily content 28 is provided according to the defined care plan, where an optional "thank you" type content element may be rendered (e.g., as shown in FIG. 19 below) indicating the character's gratitude for the patient's participation in assisting with the character's situation.

The apparatus 10 of FIG. 1 may provide the role playing simulation content 40 in the above described structured presentation, and/or may provide this content 40 on an as-selected basis for the patient, wherein suitable selection screens may be provided for the patient to select this content 40 from a menu or other selection medium. In addition, the system 10 may provide other forms and types of games to encourage patient interest in health topics and to thereby encourage active engagement and interaction. The role playing simulation characters 42 provide a friendly way for the patient to get involved in nurturing the character 42 to optimal health status, where the continuing "episodes" may be ordered or structured to have the character's situation mirror that of the patient. In this manner, the patient may adopt the character 42 as a friend going through a shared experience, and may thus become more actively engaged in their own condition and the defined care program. In this respect, the interactive role playing simulation content 42 provide both motivation and fun for the patient by challenging the user to solve problems and rehearse skills, by which the information content 28 is reinforced. Thus, the interactive simulations 40 can improve the patient's knowledge, skills, self-esteem, self-efficacy, communication and social support, health behaviors, adherence to a prescribed regimen, and health outcomes.

Referring now to FIGS. 1 and 4-19, a general description of the overall operation of the exemplary apparatus 10 is presented in the flow chart 300 of FIG. 4, wherein a care plan is initially generated at 302. Before or when the patient logs onto the apparatus 10 via the user interface 12, the display 14, and the remote control 16, the itinerary arrangement system 32 of either the server 22 or the interface device 12 organizes content at 304 for the current day's viewing by the patient into a serially arranged guided encounter. In one implementation using the arrangement system 32 of the network server 22, the server 22 arranges the day's content through generation of a guided encounter at 304 including one or more content elements 28 and transmits the plan to the user interface device 12 in advance of when it is scheduled to be viewed, or as it is to be viewed. Alternatively, the set top box interface 12 can be preloaded and delivered to the patient with a care plan already stored therein. In one embodiment, the server 22 streams content to the user interface device 12 as it is being viewed, or accesses and releases content that is preloaded or stored on the user interface device 12. In another embodiment, an itinerary arrangement processor 32 of the user interface 12 is used, where the server 22 transmits the identity of the preselected content 28 that the patient should view, and the local itinerary arrangement processor 32 in the set top box 12 arranges the content into a guided encounter. When the content 28 is stored locally on the user interface device 12, moreover, the local itinerary arrangement processor 32 takes content that is selected for the current day's viewing, and arranges it into a simple, easy to understand presentation in the form of a guided encounter to be viewed on command by the patient.

With the content elements arranged into a guided encounter for the patient at 304, the interface device 12 is prepared to present the guided encounter to the patient. The patient powers up the user interface device 12, and is presented with a welcome screen as shown in FIG. 5, and the patient logs on to the network at 306 by entering a patient identification code into a log on screen (FIG. 6) using the remote control 16, where the code prevents persons other than the patient from accessing the patient's information and programming. The user interface device 12 then presents a welcome screen as shown in FIG. 7 to the patient via the display 14 for several seconds, followed by presentation at 308 of an itinerary screen (FIG. 8), showing the day's scheduled activities. This screen gives the patient an idea of the amount of material that will be covered, where the itinerary may be summarized orally and visually by a nurse narrator and may optionally provide approximate time durations of the material to be presented such that a patient or user can schedule or plan his or her day. In the illustrated example, moreover, the itinerary screen may indicate to the user that "situation of the day" type role playing simulation content 40 will be presented as part of the day's activities.

At 310, the user interface 12 prompts the patient to begin the presentation, such as by pressing any key 18 on the remote 16 at 312. As shown in FIG. 9, an overview of the first content element is presented, such as showing the title of a video element 28 about hypoglycemia, where the overview screen may include the expected video duration, details about topics covered, etc. The patient then selects to proceed at 312 (FIG. 4), such as by pressing any key 18, and the user interface 12 renders the first content element 28 at 314, such as a hypoglycemia video depicted in FIG. 10. At 315, a determination may be made as to whether the current content element 28 is an interactive survey/quiz type element, and if not (e.g., NO at 315 for an educational content element 28), the patient may be offered the option to save the content element 28 for later review at 316 from a save screen (FIG. 11). Thereafter, the patient is returned to the itinerary screen (FIG. 12) at 318, where the screen may include check marks as shown or other indicia indicating to the patient their relative progress through the material.

The user interface device 12 makes a determination at 320 as to whether there are additional content elements 28 remaining for presentation to the patient in the guided encounter, and if so (YES at 320), returns to 310 and prompts the user to indicate when they are ready to start the next content element 28, such as by pressing any key 18 on the remote controller 16. This process continues at 310-315 as described above, wherein the next element 28 may be a survey or questionnaire or quiz element 28 in which the patient enters one or more responses (YES at 315). In one example, a survey/quiz screen may be presented which requests the patient to answer a question, in this example, after watching the hypoglycemia video. Once the patient provides answers to the survey using the remote 16, the user interface device 12 determines at 328 whether the patient response is correct. If not (NO at 328), appropriate portions of the preceding educational content element 28 may be reviewed at 330, and otherwise, (YES at 328), the user interface returns to the itinerary screen at 318. At 320, the user interface 12 again checks if there is any remaining content.

In the illustrated example, the itinerary screen then indicates that the next content element 28 is a role playing simulation 40 in the form of a "situation of the day" episode, which may have been preselected or may be selected based at least partially on the patient's response to the survey/quiz content 28. The situation is then presented to the patient as shown in FIG. 13, "Feeling Dizzy". In this implementation, moreover, the patient is optionally presented with a character selection content element shown in FIG. 14 which allows the patient to select from a first character "Mary" or a second character "Bill". As shown in FIG. 15, moreover, the selected character 42 (in this case "Mary") is then introduced to the patient, where the introduction preferably includes an image of Mary along with spoken and/or written descriptive materials about Mary. In one embodiment, the introduction can be a video of Mary introducing herself and telling the patient about her condition and other personal information. The role playing simulation content elements 40 are then rendered to the patient at 314 (FIG. 4), wherein FIG. 16 illustrates rendering of situation content to the patient (122 in FIG. 3 above) in which Mary is feeling dizzy, and the patient can continue to the next screen after reading or hearing Mary's condition. Thereafter, a question is presented to the patient (124 in FIG. 3) as shown in FIG. 17. In this example, the patient is told Mary's glucose reading and asked what Mary should do ("What should Mary do?"). In other implementations, the screen may include a picture or video of Mary asking in the first person "What should I do?" in order to engage the patient to help Mary based on information learned in the earlier educational information content. The patient then enters a response or answer (126 in FIG. 3 above), and the apparatus 10 then renders response content (at 128 in FIG. 3) to the patient as shown in FIG. 18, including an image (in this case a glass of orange juice) and text to reinforce the correct answer, even if the patient entered the wrong response. In the illustrated example, moreover, a "thank you" content element is presented in FIG. 19 indicating the character Mary's gratitude to the patient for helping the character 42 with her situation.

Figure 21:
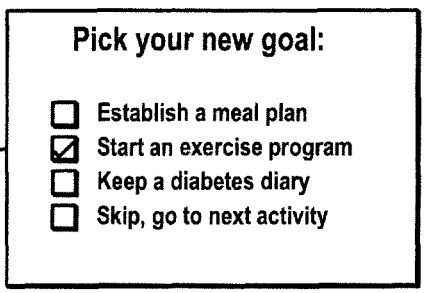
FIG. 21 is a schematic diagram illustrating an exemplary navigational menu screen rendered to a patient using the apparatus of FIG. 1.
Figure 22:
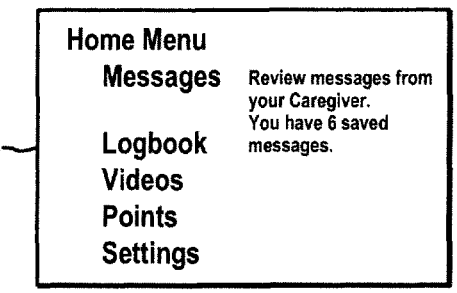
FIG. 22 is a schematic diagram illustrating an exemplary user feedback/selection screen rendered to a patient using the apparatus of FIG. 1.

Once all the scheduled content elements 28 have been presented (NO at 320 in FIG. 4), the user interface 12 displays an end dialog screen at 322 that congratulates the patient on a successful completion of the guided encounter, an example of which is shown in FIG. 20, after which the patient can press any key 18 to go to a general navigational menu at 324 (FIG. 21) allowing selection of other activities and functions of the system other than those required in the current day's itinerary, and the patient can provide the apparatus 10 with feedback on their own personal goals concerning what they would like to accomplish, as depicted in FIG. 22 or can log off at 326.

The above described examples are merely illustrative of several possible embodiments of the present disclosure, wherein equivalent alterations and/or modifications will occur to others skilled in the art upon reading and understanding this specification and the annexed drawings. In particular regard to the various functions performed by the above described components (assemblies, devices, systems, circuits, and the like), the terms (including a reference to a "means") used to describe such components are intended to correspond, unless otherwise indicated, to any component, such as hardware, software, or combinations thereof, which performs the specified function of the described component (i.e., that is functionally equivalent), even though not structurally equivalent to the disclosed structure which performs the function in the illustrated implementations of the disclosure. In addition, although a particular feature of the disclosure may have been disclosed with respect to only one of several embodiments, such feature may be combined with one or more other features of the other implementations as may be desired and advantageous for any given or particular application. Also, to the extent that the terms "including", "includes", "having", "has", "with", or variants thereof are used in the detailed description and/or in the claims, such

Having thus described the preferred embodiments, the invention is now claimed to be:

1. A health care apparatus to render audio visual content to a medical patient, comprising:
   a content element storage coupled with a communications network and adapted to store a plurality of audio visual content elements to be rendered to a medical patient as part of a defined care plan, the audio visual content elements including a plurality of role playing simulation content elements in which the patient is presented with a situation involving an issue related to a medical condition confronted by a character and in which the patient provides input related to the character's situation; and
   a user interface operatively coupled with the communications network and with a display device, the user interface being operable by the patient to render to the patient with the display device:
   selected content elements;
   a response of the role playing simulation content elements after the patient provides the input, the response including an indication of the correct input along with an image to reinforce the correct input;
   a situation introduction content element; and
   a character selection content element after the situation introduction content element.

2. The health care apparatus according to claim 1, further comprising:
   an itinerary arrangement system operatively coupled with the content element storage and adapted to:
   select one or more content elements from the content element storage including at least one role playing simulation content element to be rendered to the patient in a given viewing session as part of a defined care plan for the patient; and
   dynamically adjust the selection of the one or more content elements from a first viewing session to a second viewing session.

3. The health care apparatus according to claim 2, wherein the itinerary arrangement system selects the at least one role playing simulation content element and at least one educational content element to be rendered to the patient as part of the defined care plan in a given viewing session, and wherein the itinerary arrangement system arranges the selected content elements into a serially ordered itinerary for presentation to the patient with the role playing simulation content element presented to the patient after the educational content element.

4. The health care apparatus of claim 2, wherein the itinerary arrangement system selects a character introduction content element to be rendered to the patient before the role playing simulation content element, the character introduction content element including an image of the character and information about the character.

5. The health care apparatus of claim 4, wherein the itinerary system further selects a character situation content element to be rendered to the patient including an image of the selected character, a description of a situation involving an issue related to a medical condition confronted by the selected character; and receives input from the patient regarding a solution to the character's situation.

6. The health care apparatus of claim 1, further comprising:
   a network server coupled with the communications network and a health care professional interface operatively coupled with the network server, the health care professional interface including a content management system for uploading, versioning, and pre-viewing content elements, wherein the user interface is a set top box operatively connected to the patient's television display, and wherein the content element storage is in one of the network server and the user interface.

7. A method of rendering health care information to a patient, comprising:
   storing by at least one processor a plurality of audio visual content elements to be rendered to a medical patient, the plurality of audio visual content elements including a plurality of role playing simulation content elements in which the patient is presented with a situation involving an issue related to a medical condition confronted by a character and in which the patient provides input related to the character's situation;
   selecting by the at least one processor one or more stored content elements based at least partially on the patient's medical condition, the selected content elements including at least one role playing simulation content element to be rendered to the patient in a given viewing session as part of a defined care plan;
   arranging by the at least one processor the selected content elements into a serially ordered itinerary with the at least one role playing simulation content element arranged to correspond to a chronology of the defined care plan; and
   rendering by the at least one processor a display of the selected content elements to the patient, wherein rendering the display of the selected content elements to the patient comprises:
   rendering an educational content element about a medical topic to the patient;
   rendering a situation introduction content element to the patient after the educational content element;
   rendering a character selection content element to the patient after the situation introduction content element;
   receiving a patient's selection of a particular character;
   rendering a character introduction content element to the patient after receiving the patient's character selection;
   rendering a character situation content element to the patient including an image of the selected character, a description of a situation involving an issue related to a medical condition confronted by the selected character;
   receiving input from the patient regarding a solution to the character's situation; and
   rendering a response content element to the patient after receiving the patient's input, the response content element an indication of a correct solution along with an image to reinforce the correct solution.

8. A method for facilitating patient education regarding a medical condition, the method comprising:
   presenting educational content to a patient about a medical topic via a user interface operatively coupled with a display device that renders preselected content elements to the patient as part of a defined care plan;
   presenting a situation introduction content element to the patient via the user interface after the educational content;

presenting a character selection content element to the patient to select a character, the character selection content element presented via the user interface after the situation introduction content element; and, reinforcing the educational content by engaging the patient in a role playing simulation in which the patient provides input to the user interface to assist the selected character with a situation involving an issue related to the medical topic confronted by the selected character.

9. The health care apparatus according to claim 2, wherein the one or more content elements further include at least one interactive survey or quiz content element, wherein the at least one role playing simulation content element is selected based on a patient response to the at least one interactive survey or quiz content element.

10. The health care apparatus according to claim 3, wherein the at least one education content element consists of audio files and/or videos.

11. The healthcare apparatus according to claim 1, further including:
a display device;
at least one processor programmed to:
define the care plan by selecting one or more of the content elements based on a generic care plan template and the input from the user interface; and
control the display device to present a role playing session on the display device as part of the care plan.

12. The healthcare apparatus according to claim 11, wherein to present the role playing sessions on the display device, the processor is further programmed to:
present a situation to the patient involving an issue related to a medical condition confronted by a character;
receive input from the patient regarding a solution to the character's situation; and
present a response to the patient's input including an indication of a correct solution and an image to reinforce the correct solution.

13. The healthcare apparatus according to claim 11, wherein the processor is further programmed to control the display device to render an educational content element about a medical topic to the patient prior to the role playing session.

14. The healthcare apparatus according to claim 11, wherein the processor is further programmed to control the display device to:
render an educational content element about a medical topic to the patient;
render a situation introduction content element to the patient;
render a character selection content element to the patient after the situation introduction content element;
receive a patient's selection of a particular character;
render a character situation content element to the patient including an image of the selected character, a description of a situation involving an issue related to a medical condition confronted by the selected character;
receive input from the patient regarding a solution to the character's situation; and
render a response content element to the patient after receiving the patient's input, the response content element an indication of a correct solution along with an image to reinforce the correct solution.

15. The healthcare apparatus according to claim 1, further including a processor programmed to:
present educational content to the patient about a medical topic via a display device that renders preselected content elements to the patient as part of the defined care plan;
present a situation introduction content element to the patient via the display device after the educational content;
present a character selection content element to the patient to select a character, the character selection content element presented via the display device after the situation introduction content element; and,
reinforce the educational content by engaging the patient in a role playing simulation in which the patient provides input to the user interface to assist the selected character with a situation involving an issue related to the medical topic confronted by the selected character.

16. The healthcare apparatus according to claim 1, further including a processor programmed to:
control the content element storage to store the plurality of audio visual content elements to be rendered to the medical patient;
select one or more of the stored content elements based at least partially on the patient's medical condition, the selected content elements including at least one interactive survey or quiz content element and at least one of the role playing simulation content elements, to be rendered to the patient in a given viewing session as part of a defined care plan, the at least one role playing simulation content element selected based on a patient response to the at least one interactive survey or quiz content element;
arrange the selected content elements into a serially ordered itinerary with the at least one interactive survey or quiz content element and the at least one role playing simulation content element arranged to correspond to a chronology of the defined care plan, wherein the at least one interactive survey or quiz content element is arranged before the role playing simulation content element; and
render on the display device the selected content elements according to the serially ordered itinerary.

17. The health care apparatus according to claim 1, wherein the user interface is further operable to render to the patient with the display device a situation of the day, the situation of the day being a role playing simulation content element specifically selected for the current day by an itinerary arrangement system.

18. The health care apparatus according to claim 1, further including:
an itinerary arrangement system adapted to:
select one or more content elements from the content element storage to be rendered to the patient during a viewing session;
arrange the selected content elements to generate an itinerary for the viewing session; and
render the itinerary to the patient with the display device when the patient begins the viewing session.

19. A method of providing health care to a patient, the method comprising:
defining by a at least one processor a care plan that includes features to assist the patient with defined health issues, the defining including electronically inputting patient information for the patient into a generic care plan template;
selecting by the at least one processor one or more new content elements of the care plan based on progress in understanding of the patient regarding the defined health issues;
providing by the at least one processor a role playing session as part of the care plan;

providing a situation introduction content element of the selected content elements to the patient; and providing a character selection content element of the selected content elements after the situation introduction content element.

20. A method of rendering audio visual health care content to a medical patient, comprising:

storing by at least one processor a plurality of audio visual content elements to be rendered to a medical patient, the plurality of audio visual content elements including a plurality of role playing simulation content elements in which the patient is presented with a situation involving an issue related to a medical condition confronted by a character and in which the patient provides input related to the character's situation;

selecting by the at least one processor one or more stored content elements based at least partially on the patient's medical condition, the selected content elements including at least one interactive survey or quiz content element and at least one role playing simulation content element, to be rendered to the patient in a given viewing session as part of a defined care plan, the at least one role playing simulation content element selected based on a patient response to the at least one interactive survey or quiz content element;

arranging by the at least one processor the selected content elements into a serially ordered itinerary with the at least one interactive survey or quiz content element and the at least one role playing simulation content element arranged to correspond to a chronology of the defined care plan, wherein the at least one interactive survey or quiz content element is arranged before the role playing simulation content element;

rendering by the at least one processor a display of the selected content elements to the patient according to the serially ordered itinerary;

rendering by the at least one processor to the patient with the display device a situation of the day, the situation of the day being a role playing simulation content element specifically selected for the current day by an itinerary arrangement system;

providing a situation introduction content element of the selected content elements to the patient; and providing a character selection content element of the selected content elements after the situation introduction content element.

\* \* \* \* \*